United States Patent [19]

Banitt

[11] Patent Number: 4,497,954

[45] Date of Patent: Feb. 5, 1985

[54] CYCLOPENTANONE DERIVATIVES

[75] Inventor: Elden H. Banitt, Woodbury, Minn.

[73] Assignee: Riker Laboratories, Inc., St. Paul, Minn.

[21] Appl. No.: 551,965

[22] Filed: Nov. 15, 1983

[51] Int. Cl.³ .......................................... C07D 211/76
[52] U.S. Cl. .................................. 546/221; 549/333; 564/177
[58] Field of Search ....................................... 546/221

[56] References Cited

U.S. PATENT DOCUMENTS

| | | | |
|---|---|---|---|
| 3,655,728 | 4/1972 | Mendel | 260/473 R |
| 3,719,687 | 3/1973 | Mendel et al. | 260/326.3 |
| 3,900,481 | 8/1975 | Banitt et al. | 260/293.77 |
| 4,071,524 | 1/1978 | Banitt | 260/293.77 |
| 4,097,481 | 6/1978 | Banitt | 260/293.77 |
| 4,339,587 | 7/1982 | Banitt | 546/337 |

OTHER PUBLICATIONS

E. H. Banitt et al., Journal of Medicinal Chemistry, 20, 821–826, (1977).

Primary Examiner—Norma S. Milestone
Attorney, Agent, or Firm—Donald M. Sell; James A. Smith; Robert W. Sprague

[57] ABSTRACT

Certain substituted cyclopentanone ethylene ketal compounds, and ketones and amides derived therefrom are useful synthetic intermediates for compounds of pharmaceutical interest. A synthetic process for using the intermediates is also described.

2 Claims, No Drawings

CYCLOPENTANONE DERIVATIVES

TECHNICAL FIELD

This invention relates to substituted cyclopentane compounds and a synthetic process useful in the preparation of compounds of pharmaceutical interest.

BACKGROUND OF THE INVENTION

Esters of benzoic acid which are substituted on the aromatic ring by 1,1-dihydroperfluoroalkoxy substituents and exhibit anesthetic activity are described in U.S. Pat. No. 3,655,728. Amides of benzoic acid which are substituted on the aromatic ring by 1,1-dihydroperfluoroalkoxy substituents and exhibit antiarrhythmic activity are described in U.S. Pat. No. 3,719,687. U.S. Pat. Nos. 3,900,481, 4,071,524 and 4,097,481 describe antiarrhythmic agents including, inter alia, N-(piperidylmethyl)benzamides substituted by one or more 1,1-dihydroperfluoroalkoxy groups. Above-mentiond U.S. Pat. No. 3,900,481 discloses the compound 2,5-bis(2,2,2-trifluoroethoxy)-N-(2-piperidylmethyl)-benzamide, a particularly useful antiarrhythmic agent also known as flecainide. An article appearing in the Journal of Medicinal Chemistry, Vol. 20, pg. 821 (1977), discloses many of the compounds described in the latter patents, and also discloses various additional compounds such as 2-(2,2,2-trifluoroethoxy)-N-(2-piperidylmethyl)benzamides in which the aromatic ring is substituted in the 5-position by a non-functional group, i.e., methyl, chloro or fluoro.

U.S. Pat. No. 4,339,587 discloses 5-hydroxy-(2,2,2-trifluoroethoxy)-N-(2-piperidylmethyl)benzamide and synthetic intermediates useful in the synthesis thereof. The compound 5-hydroxy-(2,2,2-trifluoroethoxy)-N-(2-piperidylmethyl)benzamide is a metabolite of flecainide and is useful as an intermediate in the synthesis of flecainide and as an antiarrhythmic agent itself.

DETAILED DESCRIPTION OF THE INVENTION

In one aspect, the present invention relates to compounds of Formula I

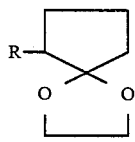
I wherein R is selected from the group consisting of

—CNH$_2$,

—CH$_2$NH$_2$,

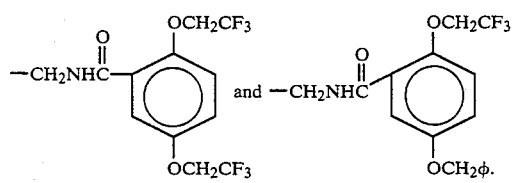

In another aspect, the present invention relates to compounds of Formula II

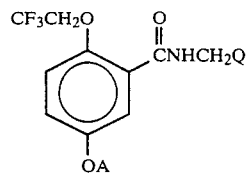
II wherein A is selected from —CH$_2$CF$_3$ and —CH$_2\phi$; and Q is selected from

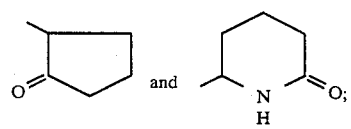

with the proviso that A is —CH$_2$CF$_3$ when Q is

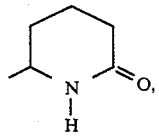

and A is —CH$_2$CF$_3$ or —CH$_2\phi$ when Q is

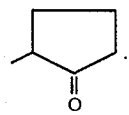

The compounds of Formulas I and II are useful as synthetic intermediates in the preparation of 5-hydroxy-N-(6-oxo-2-piperidylmethyl)-2-(2,2,2-trifluoroethoxy)-benzamide (a metabolite of flecainide) and 2,5-bis(2,2,2-trifluoroethoxy)-N-(6-oxo-2-piperidylmethyl)benzamide.

In still another aspect, the present invention relates to a process for preparing 5-hydroxy-N-(6-oxo-2-piperidylmethyl)-2-(2,2,2-trifluoroethoxy)benzamide and 2,5-bis(2,2,2-trifluoroethoxy)-N-(6-oxo-2-piperidylmethyl)benzamide using the above intermediates.

Synthetic 5-hydroxy-N-(6-oxo-2-piperidylmethyl)-2-(2,2,2-trifluoroethoxy)benzamide is useful as a standard for monitoring the metabolism of flecainide in mammals. As for 2,5-bis(2,2,2-trifluoroethoxy)-N-(6-oxo-2-piperidylmethyl)benzamide, it is believed that this compound could be reduced to provide flecainide and that it therefore is a useful synthetic intermediate.

The following reaction scheme, wherein B is benzyl or —CH$_2$CF$_3$, and B' is hydrogen (if B is benzyl) or —CH$_2$CF$_3$ (if B is —CH$_2$CF$_3$), illustrates a synthetic route by which the compounds of Formulas I and II may be obtained and the manner in which they may be used:

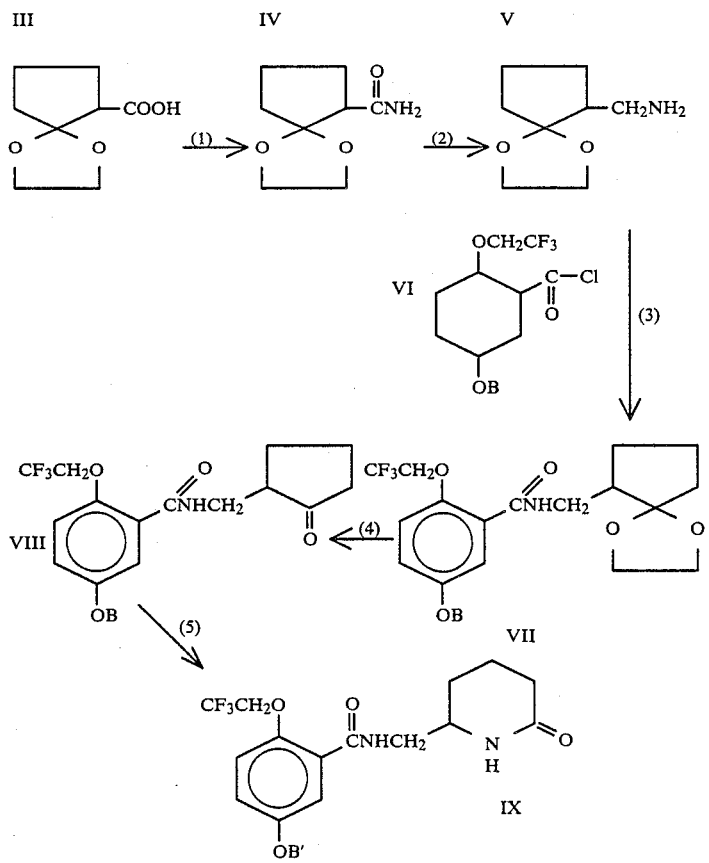

In step (1), known 2-oxocyclopentanecarboxylic acid ethylene ketal (Formula III) is converted to 2-oxocyclopentanecarboxamide ethylene ketal (Formula IV) under anhydrous conditions using a conventional mixed anhydride method. More particularly, the reactant is dissolved in a suitable inert solvent such as chloroform in the presence of an organic acid acceptor such as an organic amin (e.g., triethylamine) or an inorganic acid acceptor such as sodium carbonate or sodium bicarbonate. Ethyl chloroformate or an equivalent reactive blocking agent is added to the mixture, followed by addition of anhydrous ammonia to provide the amide of Formula IV.

Alternatively, a simple lower alkyl ester of the compound of Formula III may be reacted with alcoholic ammonia by heating in a bomb to provide the amide of Formula IV.

The amide of Formula IV is readily reduced in step (2) using a metal hydride reducing agent such as lithium aluminum hydride to provide (2-oxocyclopentane)methylamine ethylene ketal (Formula V) which may be readily converted to the amine salt by conventional methods.

In step (3) the amine of Formula V is reacted with a known compound of Formula VI by heating in an inert solvent in the presence of an organic or inorganic acid acceptor such as those described above in connection with step (1). The product of step (3) is a compound of Formula VII.

In step (4) the compound of Formula VII is converted by hydrolysis to the corresponding ketone of Formula VIII by heating in an aqueous alcohol such as aqueous ethanol in the presence of dilute strong acid such as hydrochloric acid.

In step (5) the compound of Formula VIII is reacted in a conventional Schmidt-type reaction by reacting with hydrazoic acid in the presence of sulfuric acid in an inert solvent or solvent blend such as a chloroform and benzene mixture. Under these reaction conditions, if B of the compound of Formula VIII is benzyl, B' is hydrogen in the product of Formula IX. If B of the compound of Formula VIII is 2,2,2-trifluoroethyl, B' remains trifluoroethyl.

The following examples illustrate the preparation of the compounds of the invention. All temperatures in the examples are given in degrees Centigrade.

EXAMPLE 1

Preparation of the Compound of Formula IV

To a solution of about 65 g of ammonia in 200 ml of methanol was added 20 g (0.10 mole) of ethyl 2-oxocyclopentanecarboxylate ethylene ketal. The mixture was heated at 130° C. while shaking in a bomb for about 16 hours. The mixture was then filtered and the solid residue discarded. The filtrate was evaporated, the resulting residue triturated with hexane, and the solid separated by filtration. The solid was dissolved in chloroform and passed through a chromatography column of florisil to provide 3.5 g of white solid after removal of solvent. This solid was recrystallized from toluene to provide fine white needles of 2-oxocyclopentanecarboxamide ethylene ketal, m.p. 134°–136° C. Analysis: Calculated for $C_8H_{13}NO_3$: %C, 56.1; %H, 7.65; %N, 8.2; Found: %C, 56.2; %H, 7.6; %N, 8.2.

EXAMPLE 2

Alternative Preparation of the Compound of Formula IV

To a stirred, cold (0° C.) solution of 1.72 g (0.01 mole) of 2-oxocyclopentanecarboxylic acid ethylene ketal in 35 ml of chloroform was added first 1.11 g (0.011 mole) of triethylamine and then 1.085 g (0.01 mole) of ethyl chloroformate, the latter being added in dropwise fashion. After stirring for 30 minutes, dry ammonia gas was bubbled in over about 5 minutes. A white solid separated while the mixture was stirred at about 0° C. for 30 minutes. The solid was separated by filtration and washed with chloroform, and the combined washings and filtrate were evaporated to provide a white solid residue of 2-oxocyclopentanecarboxamide ethylene ketal. Infrared spectral analysis showed the product to be identical to that obtained in Example 1.

EXAMPLE 3

Preparation of the Compound of Formula V

To a stirred suspension of 8.11 g (0.218 mole) of lithium aluminum hydride in 50 ml of diethyl ether under nitrogen was added, in small portions, 24.3 g (0.142 mole) of 2-oxocyclopentanecarboxamide ethylene ketal. The stirred mixture was heated at reflux for about one day, and the excess lithium aluminum hydride was then decomposed by adding sequentially and dropwise 8 ml of water, 12 ml of 10 percent aqueous sodium hydroxide solution, and an additional 20 ml of water. Filtration of the mixture followed by evaporation of the filtrate provided an oil. The oil was distilled to provide a clear, colorless liquid, b.p. 62°–65° C./0.4 mm of Hg, this being (2-oxocyclopentane)methylamine ethylene ketal.

To a solution of 0.5 g of the ketal in 50 ml of diethyl ether was added diethyl ether which had previously been saturated with hydrogen chloride until the mixture was acid to litmus paper. The solid was separated by filtration, washed with ether and recrystallized from acetonitrile to provide white solid (2-oxocyclopentane)methylamine ethylene ketal hydrochloride, m.p. 144°–146°C. Analysis: Calculated for $C_8H_{15}NO_2 \cdot HCl$: %C, 49.6; %H, 8.3; %N, 7.2; Found: %C, 49.4; %H, 8.4; %N, 7.1.

EXAMPLE 4

Preparation of the Compound of Formula VII

To a stirred suspension of 8.7 g (0.055 mole) of (2-oxocyclopentane)methylamine ethylene ketal, 17.6 g (0.166 mole) of sodium carbonate and 200 ml of benzene was added dropwise a solution of 19.1 g (0.0553 mole) of 5-benzyloxy-2-(2,2,2-trifluoroethoxy)benzoyl chloride in 100 ml of benzene. The mixture was then heated to reflux and maintained at reflux for one hour. The mixture was evaporated, and water and diethyl ether were added to the residue. The layers were separated, and the organic layer was washed with saturated sodium chloride solution and dried over magnesium sulfate. The organic layer was evaporated to provide an off-white residue. Recrystallization of a sample of the solid residue from 2:1 heptane:benzene with treatment with decolorizing charcoal provided 5-benzyloxy-N-[(2-oxocyclopentane)methyl ethylene ketal]-2-(2,2,2-trifluoroethoxy)benzamide, m.p. 81.5°–82.5° C. Analysis: Calculated for $C_{24}H_{36}F_3NO_5$: %C, 61.9; %H, 5.6; %N, 3.0; Found: %C, 61.9; %H, 5.6; %N, 2.8.

EXAMPLE 5

Preparation of the Compound of Formula VIII

To a solution of 24.3 g (0.0522 mole) of 5-benzyloxy-N-[(2-oxocyclopentane)methyl ethylene ketal]-2-(2,2,2-trifluoroethoxy)benzamide in 300 ml of ethanol was added 4 ml of 3N hydrochloric acid and 300 ml of water. The mixture was gradually heated to its reflux temperature and maintained at reflux for one hour. This mixture was cooled, 100 ml of water was added thereto, and the mixture was cooled with an ice bath. The white solid was separated by filtration and washed with cold water. A sample was recrystallized from 1:1 heptane-toluene to provide 5-benzyloxy-N-(2-oxocyclopentane)methyl-2-(2,2,2-trifluoroethoxy)benzamide, m.p. 105°–107° C. Analysis: Calculated for $C_{22}H_{22}F_3NO_4$: %C, 62.7; %H, 5.3; %N, 3.3; Found: %C, 62.7; %H, 5.3; %N, 3.1.

EXAMPLE 6

Preparation of the Compound of Formula IX

To a stirred, chilled (0° C.) solution of 10 ml of concentrated sulfuric acid in 120 ml of chloroform was added dropwise a solution of 15.5 g (0.0368 mole) of 5-benzyloxy-N-(2-oxocyclopentane)methyl-2-(2,2,2-trifluoroethoxy)benzamide in 40 ml of chloroform and 28 ml of a 4 molar stock solution of hydrazoic acid in toluene. Stirring was continued for 1.5 hours at 0° C. after the completion of the addition. Water (100 ml) was added to the solution, and the organic layer was separated and dried over magnesium sulfate, and then evaporated. The residue was triturated with hot toluene, and cooled. The solid was separated by filtration, recrystallized from ethyl acetate with treatment with decolorizing charcoal and cooled to provide 5-hydroxy-N-(6-oxo-2-piperidylmethyl)-2-(2,2,2-trifluoroethoxy)benzamide, m.p. 156°–158° C. Analysis: Calculated for $C_{15}H_{17}F_3N_2O_4$: %C, 52.0; %H, 4.95; %N, 8.1; Found: %C, 51.5; %H, 5.1; %N, 7.7. The structural assignment was confirmed by comparison of infrared and nuclear magnetic resonance spectra to those of the same compound prepared by an alternative synthetic procedure which is described in copending application U.S. Ser. No. 551,967, filed of even date and commonly assigned.

What is claimed is:

1. A process for preparing a compound of the formula

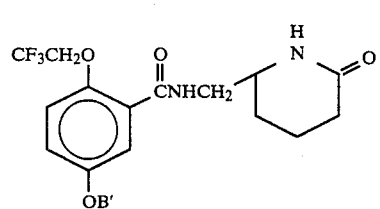

wherein B′ is hydrogen or —$CH_2CF_3$, comprising the steps of:
 (a) converting 2-oxocyclopentanecarboxylic acid ethylene ketal to 2-oxocyclopentanecarboxamide ethylene ketal;
 (b) reducing the product of step (a) to (2-oxocyclopentane)methylamine ethylene ketal;
 (c) reacting the product of step (b) with a reactant of the formula

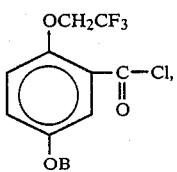

wherein B is benzyl or —CH$_2$CF$_3$, to provide a product of the formula

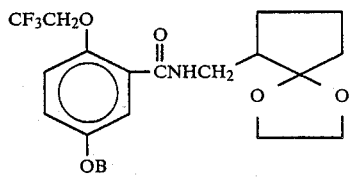

wherein B is as defined above;

(d) hydrolyzing the product of step (c) to provide a product of the formula

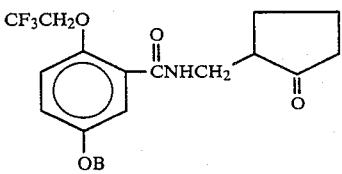

wherein B is as defined above; and (e) reacting the product of step (d) with hydrazoic acid to provide said compound;

with the provisos that when B is benzyl, step (e) provides said compound wherein B' is hydrogen, and when B is —CH$_2$CF$_3$, step (e) provides said compound wherein B' is —CH$_2$CF$_3$.

2. A process according to claim 1, wherein B is benzyl.

* * * * *